United States Patent
Schmieding et al.

(10) Patent No.: US 8,535,703 B2
(45) Date of Patent: *Sep. 17, 2013

(54) METHODS OF ARTHROSCOPIC OSTEOCHONDRAL RESURFACING

(75) Inventors: Reinhold Schmieding, Naples, FL (US); Gerlinde Michel, Munich (DE); Stephane Naudin, Planegg (DE); Hans Linden, Köln (DE)

(73) Assignee: Arthrex, Inc., Naples, FL (US)

( * ) Notice: Subject to any disclaimer, the term of this patent is extended or adjusted under 35 U.S.C. 154(b) by 807 days.

This patent is subject to a terminal disclaimer.

(21) Appl. No.: 12/198,843

(22) Filed: Aug. 26, 2008

(65) Prior Publication Data

US 2009/0060974 A1 Mar. 5, 2009

Related U.S. Application Data

(60) Provisional application No. 60/968,261, filed on Aug. 27, 2007.

(51) Int. Cl.
- *A61F 2/02* (2006.01)
- *A61K 35/16* (2006.01)
- *A61K 35/14* (2006.01)
- *A61K 35/28* (2006.01)

(52) U.S. Cl.
USPC .......................... 424/423; 424/529; 424/530

(58) Field of Classification Search
None
See application file for complete search history.

(56) References Cited

U.S. PATENT DOCUMENTS

| | | | |
|---|---|---|---|
| 2002/0156531 A1* | 10/2002 | Felt et al. | 623/17.16 |
| 2003/0212426 A1* | 11/2003 | Olson et al. | 606/191 |
| 2005/0038520 A1* | 2/2005 | Binette et al. | 623/18.11 |
| 2006/0190078 A1* | 8/2006 | Fell | 623/14.12 |

OTHER PUBLICATIONS

Thompson, D.F.; Letassy, N.A.; Thompson, G.D. Fibrin glue: a review of its preparation, efficacy, and adverse effects as a topical hemostat. The Annals of Pharmacotheraphy. Drug Intelligence & Clinical Pharmacy: vol. 22, No. 12, pp. 946-952, 1998. http://www.theannals.com/cgi/content/abstract/22/12/946 Reviewed on Jun. 15, 2011.*

* cited by examiner

*Primary Examiner* — Robert A Wax
*Assistant Examiner* — Jessica Worsham
(74) *Attorney, Agent, or Firm* — Dickstein Shapiro LLP

(57) ABSTRACT

Methods of arthroscopic resurfacing of anatomical tissue utilizing a biological component strengthened with glue or similar material. The biological component is selected from the group consisting of blood, blood components, PRP, bone marrow aspirate (BMA) and autologous conditioned plasma (ACP). The biological component/glue composition may be inserted (by injection and/or by employing a biologic resurfacing mold, for example) into, or in the vicinity of, the anatomical tissue. Upon insertion within, or contact with, the anatomical tissue, the biological component/glue composition is designed to coagulate and solidify (or partially solidify) within minutes, to advance healing or tissue growth of the anatomical tissue. The biological component/glue composition may optionally comprise components such as growth factors, antiseptic chemicals and/or antibiotics and/or electrolytes, or hormones or site-specific hybrid proteins, among others.

10 Claims, 2 Drawing Sheets

METHODS OF ARTHROSCOPIC OSTEOCHONDRAL RESURFACING

CROSS-REFERENCE TO RELATED APPLICATIONS

This application claims the benefit of U.S. Provisional Application No. 60/968,261, filed Aug. 27, 2007, the entire disclosure of which is incorporated by reference herein.

FIELD OF THE INVENTION

The present invention relates to surgical methods for resurfacing bone and cartilage defects using biological compounds.

BACKGROUND OF THE INVENTION

Joint injuries typically involve damage to the bones and/or tendons that form the joint. This damage can range from bone chips to tears to simple wear. In the case of bone chips or wear, it is often necessary to repair the damage by replacing the missing bone material. This has been typically accomplished by attaching an implant over the defect that replicates the original bone structure.

A promising method of repairing bone damage is the use of platelet-rich plasma (PRP). PRP is obtained from the blood of blood donors. Previous studies have mixed PRP with a demineralized bone matrix, placed the resulting compound in a capsule, and then inserted the capsule near the bone in need of repair. Unfortunately, these studies have found the process to be largely unsuccessful at rebuilding bone structure.

Other features and advantages of the present invention will become apparent from the following description of the invention, which refers to the accompanying drawings.

BRIEF SUMMARY OF THE INVENTION

Figure 1:
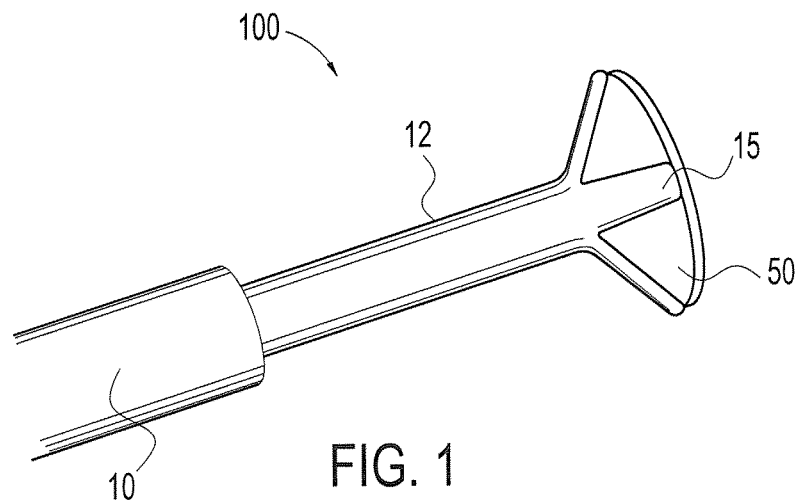
FIG. 1 illustrates a perspective view of an umbrella device, in an expanded configuration, used for antegrade advancement of biological components strengthened with glue, according to an embodiment of the present invention.

The present invention relates to methods of arthroscopic resurfacing utilizing biological components strengthened with a glue (for example, a bioglue, Cohera glue, an amino acid glue, fibrin glue, or hydrogels, among others). The biological component is selected from the group consisting of blood, blood components or fractions, PRP, bone marrow aspirate (BMA) and autologous conditioned plasma (ACP). The biological component/glue composition may be provided (by injection or by employing a biologic resurfacing mold, for example) directly into the arthroscopic site or into the anatomical tissue, or in the vicinity of the arthroscopic site or tissue to be repaired. The biological component/glue composition coagulates and solidifies (or partially solidifies) within minutes, to advance the healing of the damaged tissue and/or tissue growth.

Other features and advantages of the present invention will become apparent from the following description of the invention, which refers to the accompanying drawings.

DETAILED DESCRIPTION OF THE INVENTION

The examples provided below detail the preferred embodiments of the present invention. Other features, embodiments, and advantages of the invention beyond those discussed in the detailed description will be obvious to those skilled in the art. Those skilled in the art should appreciate that many changes may be made to the present invention without departing from the scope or spirit of the present invention.

The present invention relates to methods of arthroscopic resurfacing of a joint utilizing a biological component (selected from the group consisting of blood, blood components or fractions, PRP, ACP and BMA) strengthened with glue or a similar material (for example, a bioglue, Cohera glue, an amino acid glue, fibrin glue, or hydrogels, among others). The biological component/glue composition may be optionally employed in conjunction with a biologic resurfacing mold (for example, a metal or plastic cap or an implant) provided with at least one channel, slot or inner hole through which the biological component/glue composition may be injected at the repair site. Once the biological component/glue composition has sufficiently coagulated and solidified, the biologic resurfacing mold may be removed and the process may be repeated at the location of other defects.

In an exemplary and illustrative embodiment only, the biological component/glue composition is a PRP/fibrin glue composition or "cocktail," which is a stable biological compound that can be injected into/through a transosseous tunnel (for example, tibial or femoral tunnel), in the vicinity of the defect to be repaired, and that can be further forced under pressure to securely contact the defect. Upon insertion at the defect site, the PRP/fibrin glue composition coagulates and solidifies within minutes, to advance the healing of the damaged tissue and tissue growth. Preferably, the PRP/fibrin glue composition is an autologous PRP/fibrin glue composition.

The present invention also provides a method of enhancing the healing of damaged tissue at an arthroscopic resurfaced site. The method comprises the steps of: (i) providing a mixture of a biological component (selected from the group consisting of blood, blood components or fractions, PRP, ACP and BMA) and glue (such as a bioglue, hydrogels, or an amino acid glue); (ii) injecting the biological component/glue mixture through an arthroscopic portal at an arthroscopic site (i.e., the arthroscopic resurfaced site); and (iii) optionally solidifying the biological component/fibrin glue mixture. The step of injecting the biological component/glue mixture through the arthroscopic portal may further and optionally comprise the steps of: providing a biologic resurfacing mold (for example, a cap or a clear umbrella device) over the arthroscopic site (for example, a prepared osteochondral socket); expanding the mold to fully cover the diameter of the osteochondral socket; and injecting the biological component/glue mixture through at least a channel, passage or slot provided within the mold.

The biological component/glue composition or "cocktail" of the present invention is preferably an autologous composition which may optionally comprise additional components such as growth factors, additional antiseptic chemicals and/or antibiotics and/or electrolytes, or hormones or site-specific hybrid proteins (that promote or enhance the wound healing effectiveness of the growth factors), among others.

Growth factors may comprise proteinaceous factors, for example, which play a role in the induction or conduction of growth of tissue, ligaments, bone, cartilage or other tissues associated with bone or joints. In particular, the following growth factors contained in platelets are set forth below (and their effects):

PDGF (Platelet-derived growth factor)—Stimulates collagen synthesis, the formation of blood vessels and fibroblast proliferation; activation of macrophages and neutrophiles; activates TGF-β; attracts stem cells.

FGF (Fibroblast growth factor)—Stimulates the formation of blood vessels, collagen synthesis, wound contraction, matrix synthesis, epithelialisation.

TGF-β (Transforming growth factor β)—Reduces scar formation; reduces wound healing disturbances caused by corticoids; attracts fibroblasts and promotes their proliferation; stimulates collagen synthesis; promotes the secretion of FGF and PDGF by monocytes.

TGF-α (Transforming growth factor-α)—Stimulates mesenchymal, epithelial and endothelial cells.

EGF—(Epithelial Growth Factor)—Stimulates re-epithelialisation, the formation of new blood vessels and collagenase activity.

The biological component/glue composition or "cocktail" of the present invention is designed to have a viscosity that allows it to be injected at the repair site and to further adhere to the resurfaced tissue (bone, ligament or cartilage) and solidify within minutes, preferably within about 1 to about 5 minutes, more preferably within about 2 minutes. In particular embodiments, the biological component/glue composition or "cocktail" may be injected through a slot or channel of a biologic resurfacing mold (for example, a cap or a clear umbrella device, preferably made of plastic) that is placed over a prepared osteochondral socket and expanded to fully cover the diameter of the osteochondral socket. The biological component/glue mixture is inserted or injected through the channel or slot provided within the mold.

Figure 2:
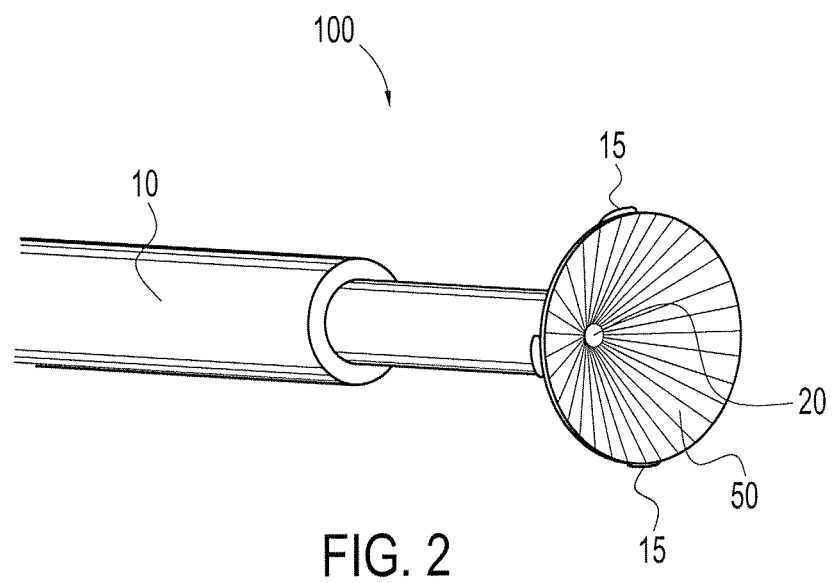
FIG. 2 illustrates another perspective view of the umbrella device of FIG. 1.
Figure 3:
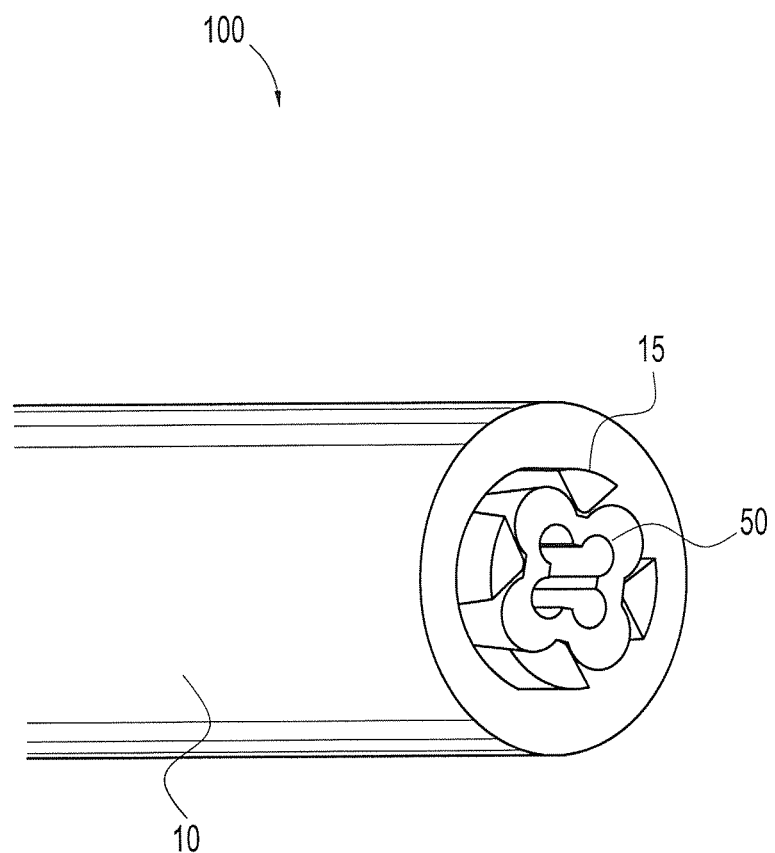
FIG. 3 illustrates a perspective view of the top of the umbrella device of FIG. 1, in a retracted configuration.

An exemplary and illustrative-only embodiment of a mold or umbrella device 100 of the present invention is illustrated in FIGS. 1-3. The device 100 comprises an outer member or sleeve 10 that houses an inner member or tube 12, which may be configured to be inserted through an arthroscopic portal. The distal end of inner member 12 terminates in a plurality of prongs 15 which are configured to engage and secure a skirt or clear umbrella 50. Skirt or umbrella 50 may preferably be made of plastic (or similar translucent and/or transparent materials) and allows the biological component/glue composition of the present invention (once it has reached the resurfaced tissue (for example, bone, ligament or cartilage)) to solidify, or to partially solidify, within minutes.

In use, device 100 is brought in the vicinity of the arthroscopic site (for example, a resurfaced site) in the retracted or folded configuration, as shown in FIG. 3. Actuating the inner member 12 from a first position (e.g., the retracted position shown in FIG. 3) to a second position (e.g., an extended or expanded position, as shown in FIGS. 1 and 2) allows umbrella 50 to move from the retracted or folded configuration (for example, a fully-retracted or folded position) to an expanded or open configuration (for example, a fully-expanded configuration).

Cannulation 20 (FIG. 2) of the inner member 12 allows the biological component/glue composition of the present invention to be injected and/or inserted through the inner member 12, to allow the biological component/glue composition to reach the resurfaced tissue (bone, ligament or cartilage). Umbrella 50 is next expanded over the resurfaced tissue and over the biological component/glue composition, contacting at least part of the biological component/glue composition and allowing the biological component/glue composition to start solidifying, or partially solidifying. Once the biological component/glue composition is partially or totally solidified, umbrella 50 (together with corresponding prongs 15) may be retracted or folded (i.e., by pulling away the inner member 12 and prongs 15) from the arthroscopic site.

The use of the composition or "cocktail" of the present invention (comprising a biological component (selected from the group consisting of blood, blood components or fractions, PRP, ACP and BMA) strengthened with glue or a similar material will be described below with reference to particular applications, i.e., hip resurfacing, patella resurfacing, and OATS resurfacing, for example. For all these exemplary arthroscopic applications, the invention provides a basic system (Cartilage resurfacing System) that includes a glue "cocktail," arthroscopic drill guides, cutters from 5-10 in mm increments and 10 to 30 mm in 5 mm diameter increments, implant retrograde insertion drivers, fixation back up options and disposable products for biologic resurfacing alternatives (such as the biologic resurfacing mold or cap of the present invention).

Femoral Condyle Focal Defect Resurfacing—Surgical Technique

A focal defect is identified arthroscopically and alternative prosthetic and biologic treatment options are evaluated. The arthroscopic Cartilage Resurfacing System of the present invention provides a single arthroscopic surgery treatment with minimum morbidity as an option to current resurfacing treatments including prosthetic replacement. In an older patient group, a prosthetic replacement may be selected with the advantage of immediate motion and partial weight bearing post op. An arthroscopic drill guide places a guide pin into the center of the defect from a retrograde approach, for example. The guide pin is replaced with the appropriate sized retrograde drill. If limited joint space restricts final size insertion, sequential insertion of smaller cutters to enlarge the socket may facilitate "around the rim" insertion of larger diameter flip cutters. The drill removes the remaining cartilage and debrides the subchondral bone prior to implant insertion.

The appropriate sized implant is inserted through an arthroscopy portal or small incision at about 90 degree angle to the drilling diameter. The drill is removed and replaced with the retrograde implant driver. The implant is attached to the driver with the implant grasper and the implant is screwed (in a retrograde manner) until the porous back of the implant is flush to subchondral bone and the implant periphery is even or below the remaining cartilage rim to avoid articulating impingement.

Fixation back up with a suture-button construct (comprising a flexible loop of suture attached to a button) attached to a fixation implant similar to the driver attachment, may be inserted through the pin cannulation into the back of the threaded screw cannulation to engage the implant. UHWMP sutures are tied over the button under controlled tension with the suture tensioner as back up fixation for the implant if desired by the surgeon.

Extended Femoral Condyle Resurfacing—Surgical Technique

The arthroscopic drill guide places the first guide pin in the extended oval shaped defect approximately 5 mm from the posterior border of the defect. A parallel guide sleeve with about 10 mm space increments is attached onto the shaft of the first pin, and a second pin is drilled (in a retrograde manner) into the defect. The guide pins are sequentially replaced by the appropriate diameter retrograde drill, and two sockets are drilled to the appropriate depth of the oval shaped femoral implant. The bone bridge between the two sockets is removed with an arthroscopic bur (such as a bur with depth stop hood). An articulating implant trial confirms the size, shape and depth of the oval socket prior to implant insertion.

The implant is inserted with two rotating threaded cage screw posts (similar to the Partial Eclipse engaging the Partial Eclipse retrograde drivers). Back up fixation with suture-button construct (implant Tightropes) is secured to both posts if desired.

Tibial Resurfacing—Surgical Technique

Surgical steps through the tibial plateau in a retrograde fashion are repeated as described for femoral resurfacing. UHMWE implants with metal backing are used in conjunction with femoral implants. Back up Tightrope fixation options may be employed.

Optional antegrade preparation of the tibial socket may be carried out from a transfemoral approach utilizing antegrade cutting drills. This ensures precise articulating contact between implants when resurfacing femoral and tibial surfaces simultaneously.

Patella Resurfacing—Surgical Technique

Surgical steps similar to femoral condyle resurfacing are repeated using a concave implant of the present invention, to anatomically recreate the undersurface of the patella and to minimize contact to the trochear groove through ROM.

Hip Resurfacing—Surgical Technique

Surgical steps for femoral condyle resurfacing are repeated. Acetabular lesions may be treated with antegrade socket creation with antegrade cutting drills from a transfemoral approach.

Biologic Resurfacing Options

After socket preparation as described for implant resurfacing, a biologic resurfacing cap is inserted through the appropriate arthroscopic portal and placed over the prepared osteochondral socket. The outer tube of the instrument is retracted allowing a clear, plastic umbrella like cap to expand by resiliency to the appropriate diameter and is placed fully over the prepared socket. A biologic cocktail of autologous components (such as blood, blood components or fractions, PRP, ACP and BMA) is mixed with glue (or a similar material) and inserted with a syringe and needle through the retrograde transosseus pin tunnel into the defect. The clear, plastic umbrella has the appropriate concave undersurface to mold the biologic cocktail to the appropriate anatomic height, curvature and configuration in the defect during the solidification period of a few minutes with arthroscopic viewing and injection control through the clear cap. The umbrella can be carefully articulated over the biologic repair to smooth out any remaining impinging areas prior to removal. Disposable biologic resurfacing caps can be produced at about 180 degree and about 90 degree handle angles as required by arthroscopy portals and defect locations.

OATS Resurfacing Options

Retrograde or antegrade sockets are drilled with drills to the appropriate depth. OATS™ plugs are harvested or allograft plugs prepared and a 4 mm Corkscrew FT™ anchor inserted into the boney base of the graft. FiberWire sutures are passed through the socket and transosseous pin tunnel with a microlasso and the plug extruded into the joint with the OATS™ delivery tube. The plug is pulled into the socket with sutures and the plug secured by tying over the opposite cortex with a two hole titanium button.

If the biological component/glue composition or "cocktail" of the present invention comprises ACP, the ACP may be obtained from blood from the patient, which is separated using a centrifuge, for example, to retrieve certain healing components such as growth factors, to obtain the ACP. Preferably, the ACP has a platelet concentration factor of about 2 compared to the platelet concentration of the patient's normal blood. For example, the ACP may contain about 470,000 platelet/microliter (for a donor) compared to the about 200,000 platelet/microliter of the donor's whole blood, and compared to the about 500,000-1,000,000 platelet/microliter of the platelet-rich plasma (PRP) (of the donor), and compared to about 0 platelet/microliter of the platelet-poor plasma (PPP) (of the donor).

The ACP may also comprise autologous growth factors as defined above. In a preferred embodiment, the term "growth factor" includes autologous growth factors produced from a patient's own blood, obtained by a centrifugation process. Optionally, the ACP may comprise additional antiseptic chemicals and/or antibiotics and/or electrolytes. The additional antiseptics and/or the antibiotics and/or the electrolytes will typically be present in the plasma in a predetermined concentration range, which will be dependent upon the particular tissue site and application, as well as the specific activity of the antiseptic and/or the antibiotic and/or the electrolytes. The antibiotics may be selected from the group consisting of a neosporin, vancomycin and gentamycin, and combinations thereof.

The ACP may further comprise one or more additional components which promote or enhance the wound healing effectiveness of the autologous growth factors. As such, hormones or site-specific hybrid proteins may be incorporated in the autologous blood suspension to maximize the availability of the autologous growth factors at the tissue to be repaired and/or to potentiate wound healing.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A method of arthroscopic osteochondral resurfacing treatment of a defect at an arthroscopic site, comprising:
   providing a biological component/glue composition comprising a biological component and glue, the biological component being selected from the group consisting of blood, blood components, platelet-rich plasma, autologous conditioned plasma and bone marrow aspirate;
   providing a resurfacing mold through an arthroscopic portal in the vicinity of the defect at the arthroscopic site in a retracted or folded configuration, the resurfacing mold comprising an outer member that houses an inner member, the inner member including a cannulation and terminating in a plurality of prongs, the prongs being configured to engage and secure a skirt or umbrella;
   retracting the outer member of the resurfacing mold to allow the skirt or umbrella to expand to an extended or expanded configuration, and securing the resurfacing mold to the defect of the arthroscopic site;
   inserting the biological component/glue composition through the cannulation of the inner member of the resurfacing mold so that the biological component/glue composition reaches the defect and lies between the resurfacing mold and the arthroscopic site; and
   subsequently, allowing the biological component/glue composition to solidify or partially solidify, the resurfacing mold having a concave undersurface to mold the biological component/glue composition to appropriate anatomic height, curvature and configuration of the defect during the solidification or partial solidification.

2. The method of claim 1, wherein the arthroscopic site is selected from the group consisting of femoral condyle, tibial plateau, patella, hip acetabulum, acromioclavicular joint and elbow joint.

3. The method of claim 1, wherein the solidified or partially-solidified composition is secured to the arthroscopic site with additional glue.

4. The method of claim 1, wherein the step of solidifying the biological component/glue composition takes place in about 1 to about 5 minutes.

5. The method of claim 4, wherein the step of solidifying the biological component/glue composition takes place in about 2 minutes.

6. The method of claim 1, wherein the step of applying the biological component/glue composition to the arthroscopic site further comprises injecting the biological component/glue composition into the arthroscopic site.

7. The method of claim 1, wherein the glue is a biological glue.

8. The method of claim 1, wherein the biological component/glue composition comprises autologous conditioned plasma, and wherein the autologous conditioned plasma is obtained by subjecting blood to at least one rotational step to obtain the autologous conditioned plasma.

9. The method of claim 1, wherein the arthroscopic site is a joint repair site adjacent a transosseous tunnel or socket.

10. The method of claim 1, wherein the arthroscopic site is damaged cartilage.

\* \* \* \* \*